US012797256B2

(12) United States Patent
Guillet

(10) Patent No.: US 12,797,256 B2
(45) Date of Patent: Nov. 17, 2026

(54) ELBOW AND FOREARM SUPPORT BRACE

(71) Applicant: Michael Sean Guillet, Cerniat (CH)

(72) Inventor: Michael Sean Guillet, Cerniat (CH)

( * ) Notice: Subject to any disclaimer, the term of this patent is extended or adjusted under 35 U.S.C. 154(b) by 0 days.

(21) Appl. No.: 19/316,862

(22) Filed: Sep. 2, 2025

(65) Prior Publication Data

US 2026/0060846 A1 Mar. 5, 2026

Related U.S. Application Data

(60) Provisional application No. 63/689,515, filed on Aug. 30, 2024.

(51) Int. Cl.
*A61F 13/10* (2006.01)
*A61B 5/296* (2021.01)

(52) U.S. Cl.
CPC ............ *A61F 13/108* (2013.01); *A61B 5/296* (2021.01)

(58) Field of Classification Search
CPC ...... A61F 5/0104; A61F 5/0118; A61F 5/013; A61F 5/05858; A61F 5/05866; A61F 5/3723; A61H 23/00–04
See application file for complete search history.

(56) References Cited

U.S. PATENT DOCUMENTS

| | | | |
|---|---|---|---|
| 3,970,081 A | 7/1976 | Applegate et al. | |
| 4,191,373 A | 3/1980 | Lancellotti | |
| 4,763,901 A | 8/1988 | Richter et al. | |
| 5,063,913 A | 11/1991 | Nyi et al. | |
| 5,759,165 A | 6/1998 | Malewicz | |
| 6,093,164 A * | 7/2000 | Davis | A61H 23/0263 602/61 |
| 6,179,751 B1 | 1/2001 | Clears et al. | |
| 11,179,263 B1 * | 11/2021 | Cofer | A61F 5/013 |
| 11,896,545 B2 * | 2/2024 | Merino | A61H 1/006 |
| 2012/0004586 A1 | 1/2012 | Martino et al. | |
| 2014/0060547 A1 | 3/2014 | Vallino et al. | |
| 2020/0360169 A1 | 11/2020 | Kelly et al. | |
| 2024/0398601 A1 * | 12/2024 | De Lange | A61F 5/013 |
| 2025/0360018 A1 * | 11/2025 | Sheiner | A61F 5/013 |

FOREIGN PATENT DOCUMENTS

| | | |
|---|---|---|
| KR | 20230076352 A | 5/2023 |
| WO | 2018180399 A1 | 10/2018 |

* cited by examiner

*Primary Examiner* — Kari K Rodriquez

(57) ABSTRACT

The present invention is a biarticular forearm support brace comprising a hand wrap, an arm wrap, vibrational motors, and EMG sensors. In the preferred embodiment of the present invention, the present invention further comprises medical-grade materials with elastic properties and a plurality of straps. The present invention takes the tension off the extensor muscles in the forearm by pulling the hand towards the elbow, replacing muscle function and allowing the extensor muscles in the forearm to be shortened while not being contracted.

18 Claims, 13 Drawing Sheets

ELBOW AND FOREARM SUPPORT BRACE

FIELD OF THE INVENTION

The present invention relates generally to medical arm support devices. Particularly, the present invention relates to an elbow support brace for users experiencing soft tissue problems such as tennis elbow, golfer's elbow, also called medial epicondylitis, or radial tunnel syndrome.

BACKGROUND OF THE INVENTION

The role of the hand is crucial for the performance of daily activities. Ensuring a full and autonomous movement is important. The hand is controlled by a complex musculo-skeletal system which extends from the elbow through the forearm and into the hand. People with soft tissue problems such as tendinitis, elbow pain, periosteum inflammation, burning sensations, tennis elbow, golfer's elbow, or radial tunnel syndrome may not have full or comfortable use of the hand and arm. Tennis elbow, for example, is tendinitis resulting from excess use of the extensor muscles in the forearm which connect the hand to the elbow.

An objective of the present invention is to provide relief for these and other related conditions. The present invention further seeks to overcome problems with prior art, namely, that the prior art only concentrates on the elbow and not the hand, making existing braces monoarticular. The prior art fails to connect the length of the muscle groups, making it impossible to release muscle activity. There exists a need to provide a support brace that connects the length of the muscle along the hand and elbow.

SUMMARY OF THE INVENTION

The present invention is a biarticular forearm support brace that releases tension from the extensor muscle group using elastic-type materials. It includes an element at the insertion of the extensor muscle in the hand and an element at the termination of the extensor muscles around the elbow, passing through both articulations.

DETAILED DESCRIPTION OF THE INVENTION

Figure 1:
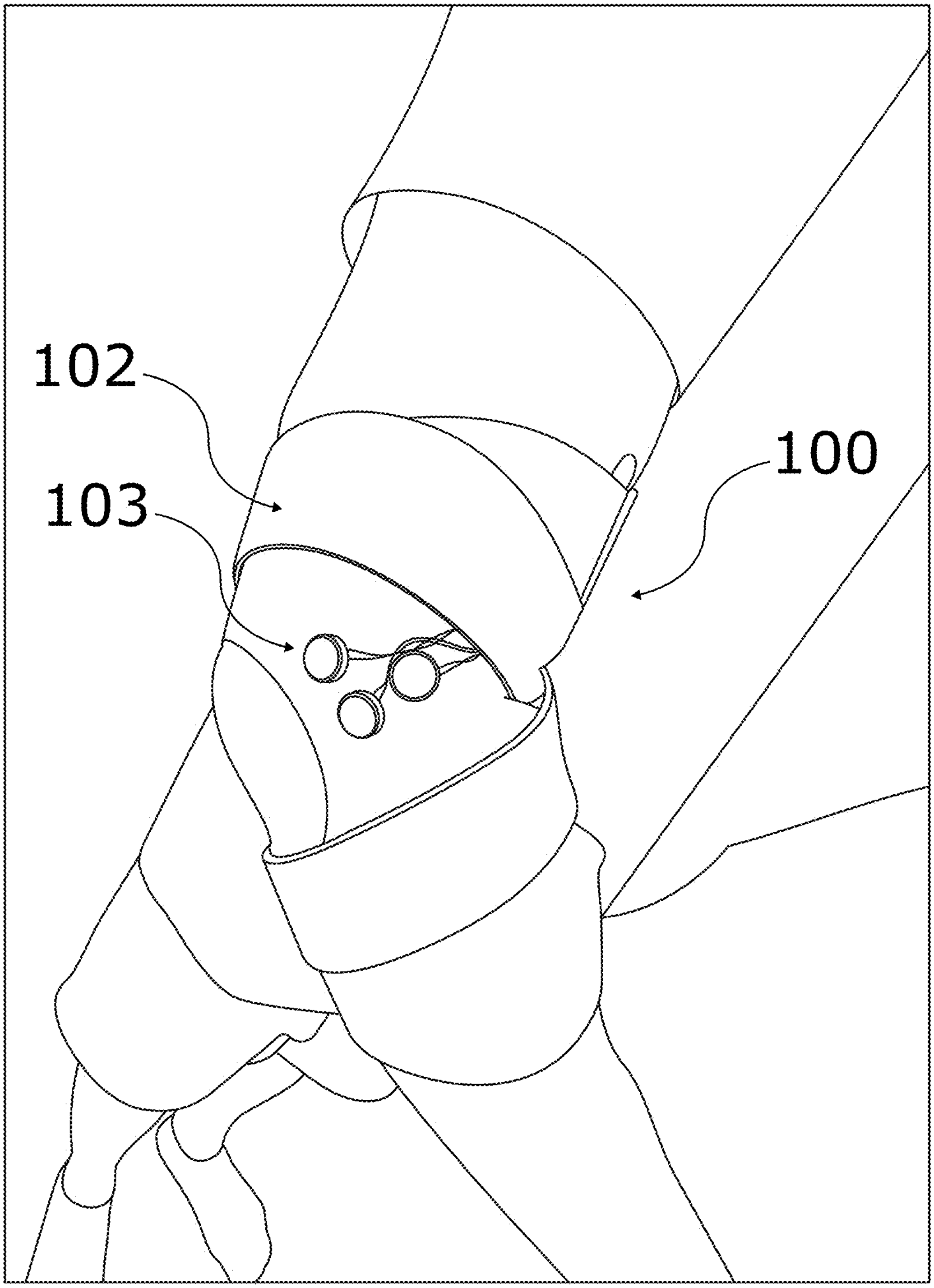
FIG. 1 is a view of the elbow brace portion of the present invention wrapped around a user's arm.
Figure 2:
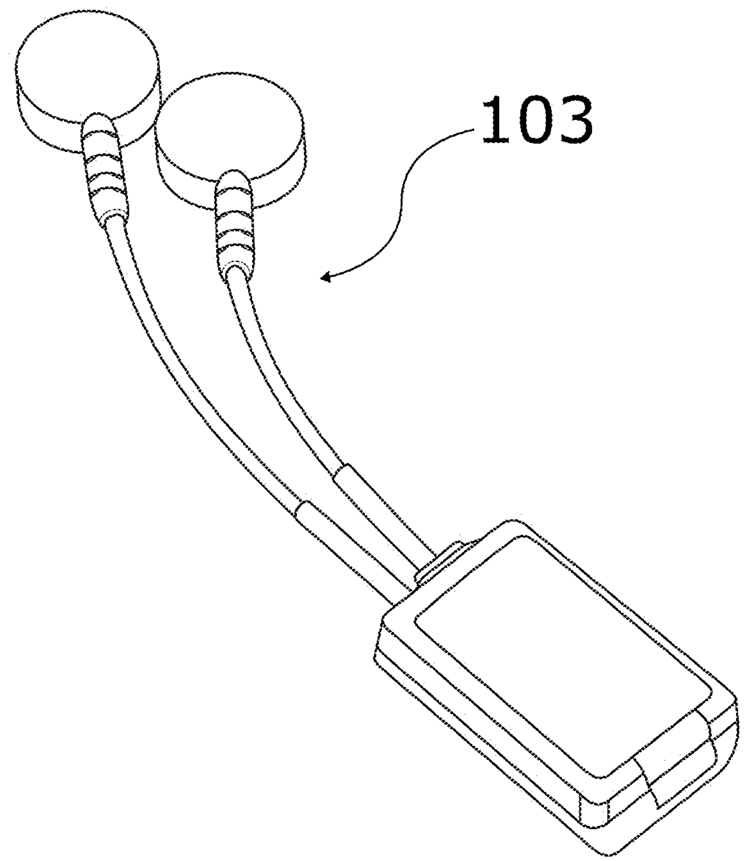
FIG. 2 shows a wireless electromyograph (EMG) which measures muscle contraction and may connect to a Bluetooth device.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header. All illustrations of the drawings are for the purpose of describing selected versions of the present invention and are not intended to limit the scope of the present invention.

The present disclosure includes many aspects and features. Moreover, while many aspects and features relate to, and are described in the context of the disclosed use cases, embodiments of the present disclosure are not limited to use only in this context.

As shown in FIG. 1-13, the present invention 100 is a biarticular forearm support brace comprising a hand wrap 101, an arm wrap 102, vibrational motors 103, and EMG sensors 104. In the preferred embodiment of the present invention, the present invention further comprises medical-grade materials with elastic properties and a plurality of straps. The present invention takes the tension off the extensor muscles in the forearm by pulling the hand towards the elbow, replacing muscle function and allowing the extensor muscles in the forearm to be shortened while not being contracted.

Figure 5:
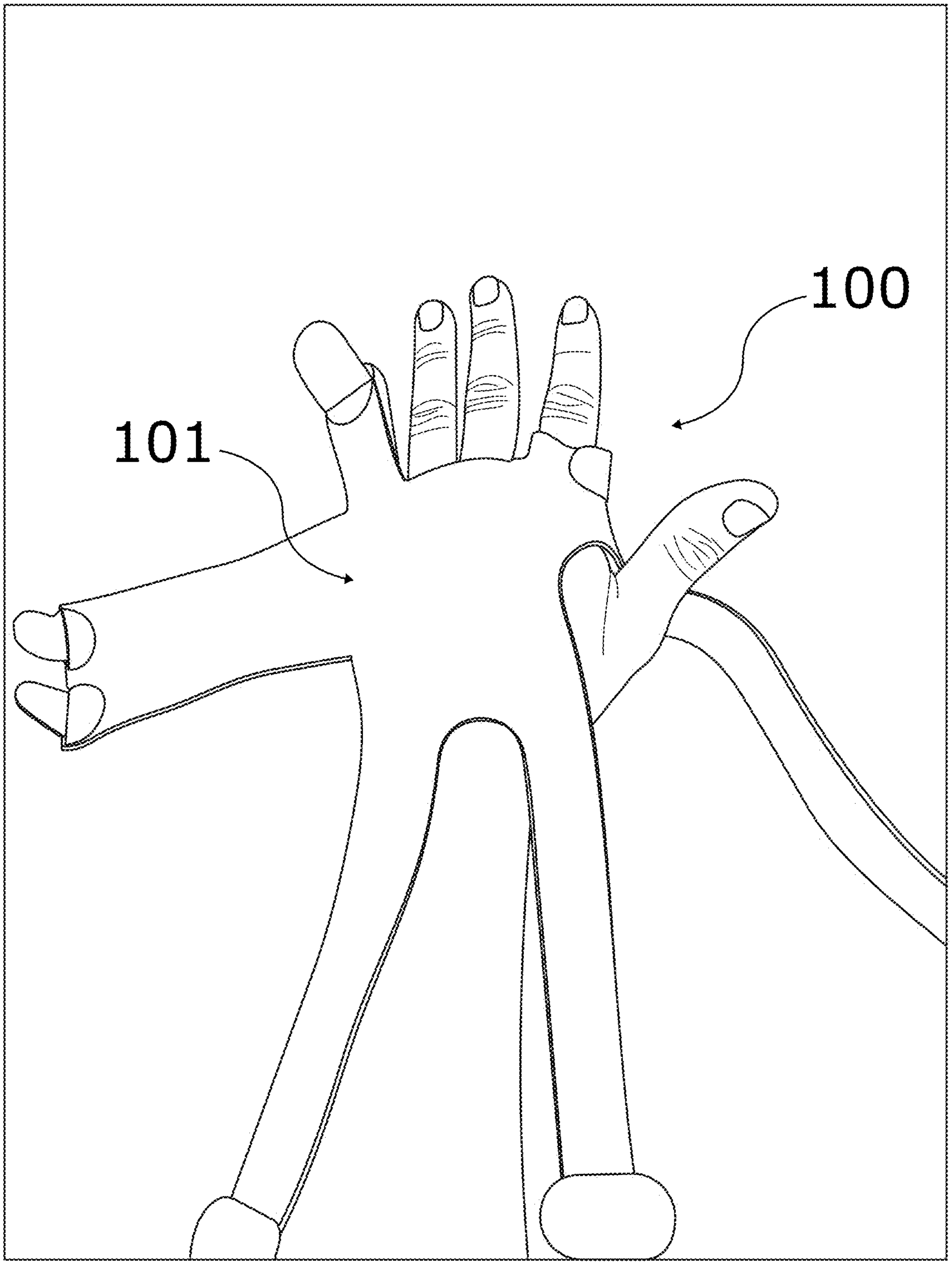
FIG. 5 shows the present invention being wrapped around a user's hand.
Figure 6:
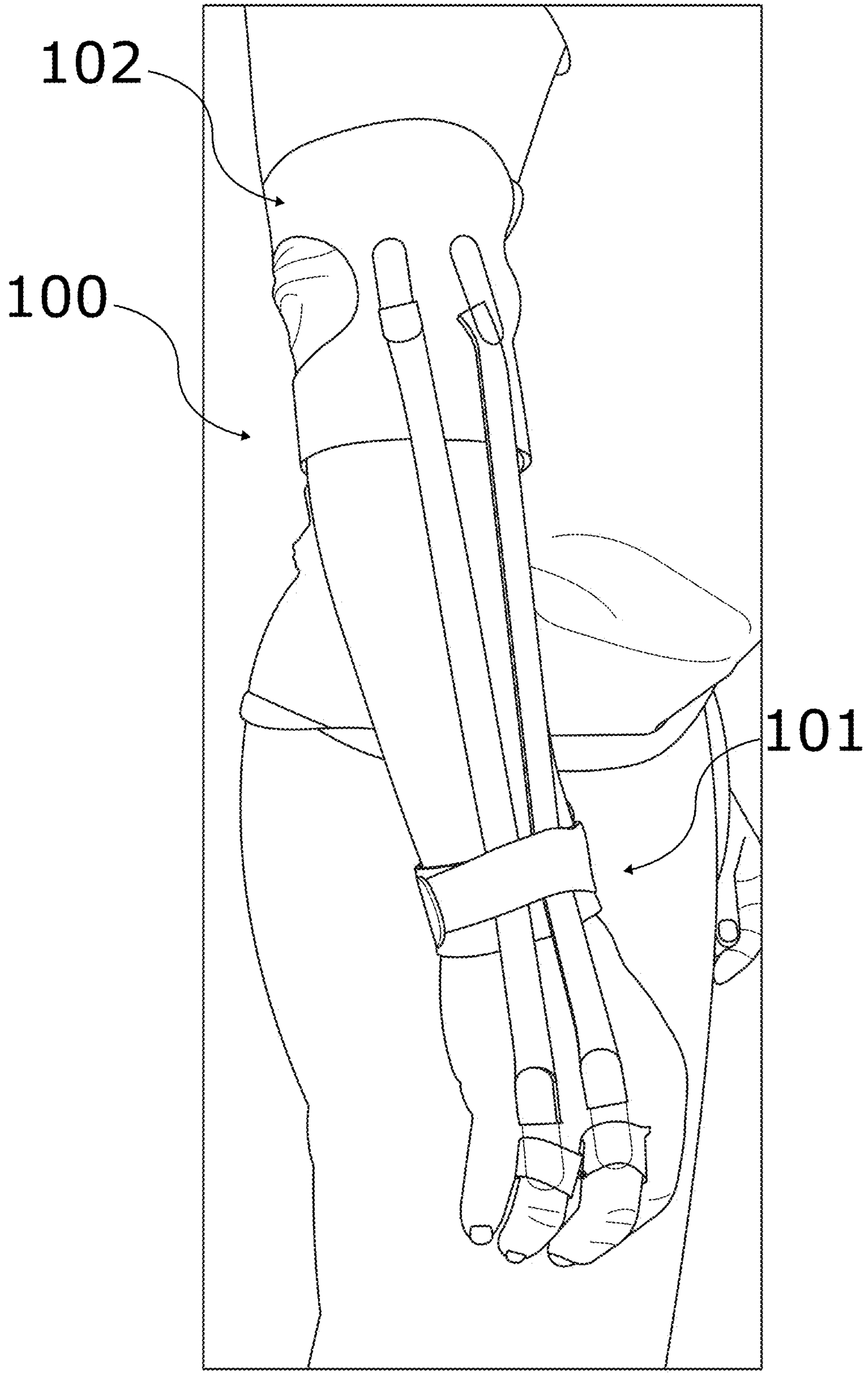
FIG. 6 is a side view of the present invention showing the straps connection the elbow and hand sections.
Figure 7:
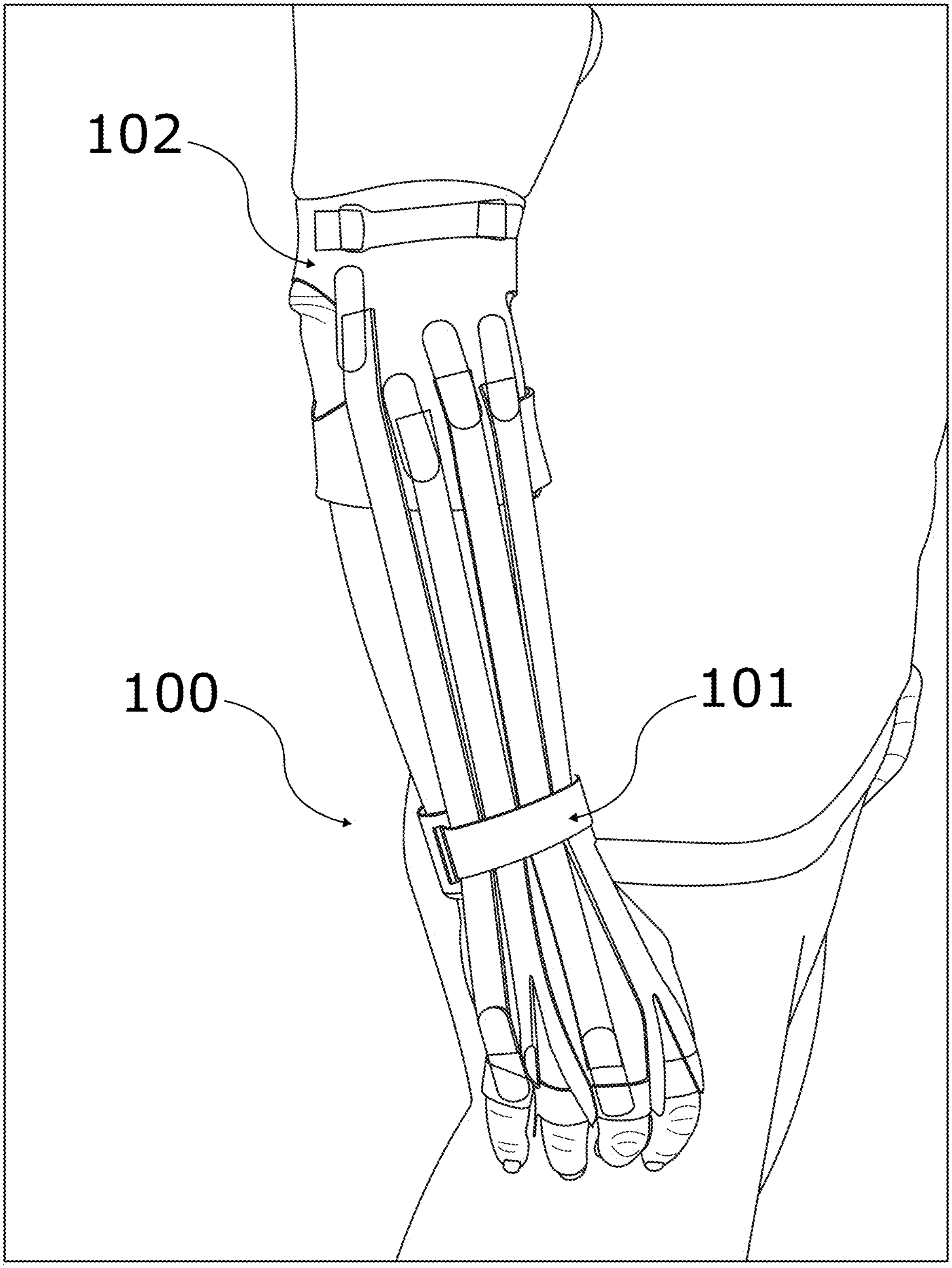
FIG. 7 is a top arm view of the present invention.
Figure 8:
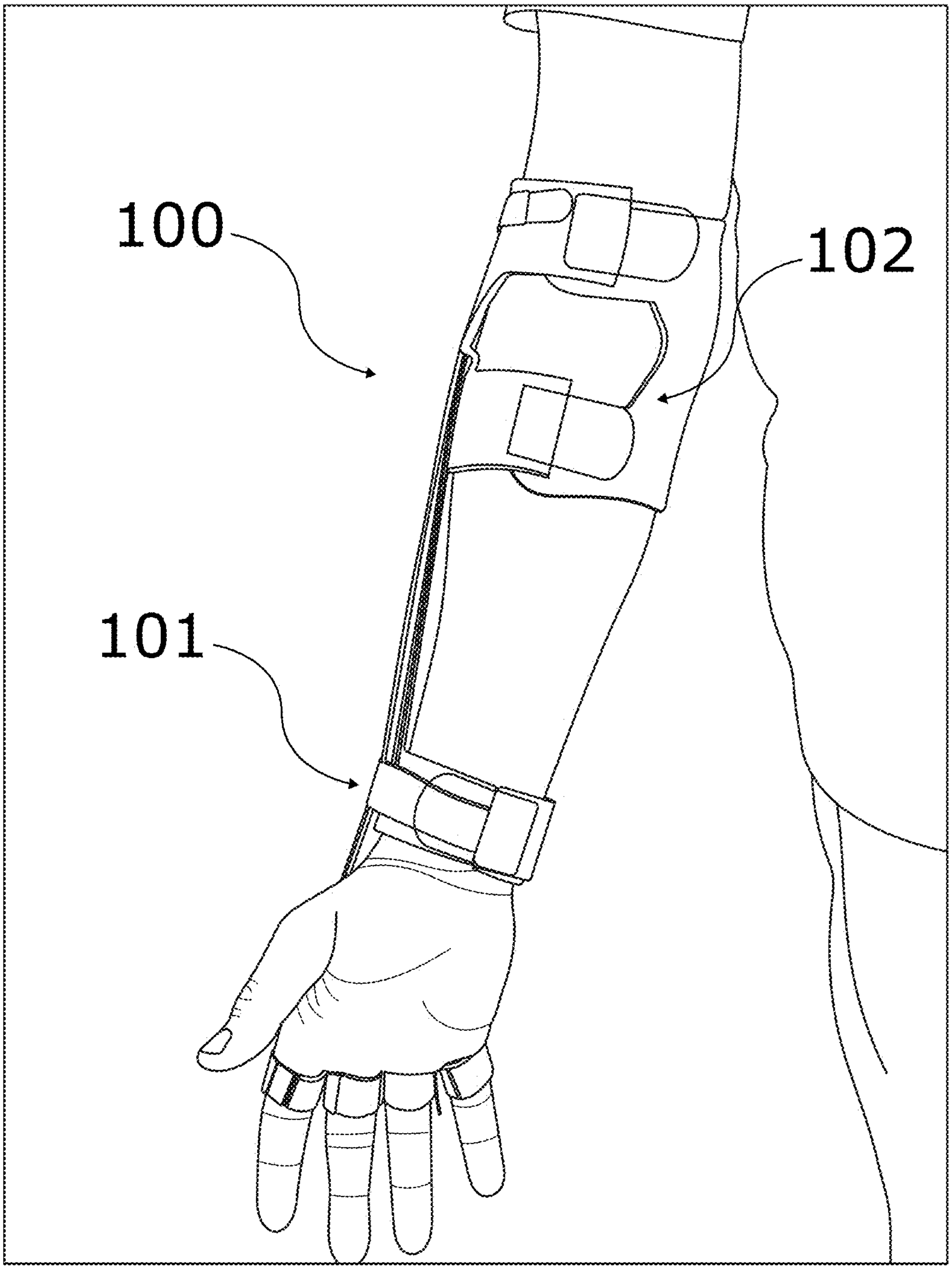
FIG. 8 is an under-arm view of the present invention.
Figure 9:
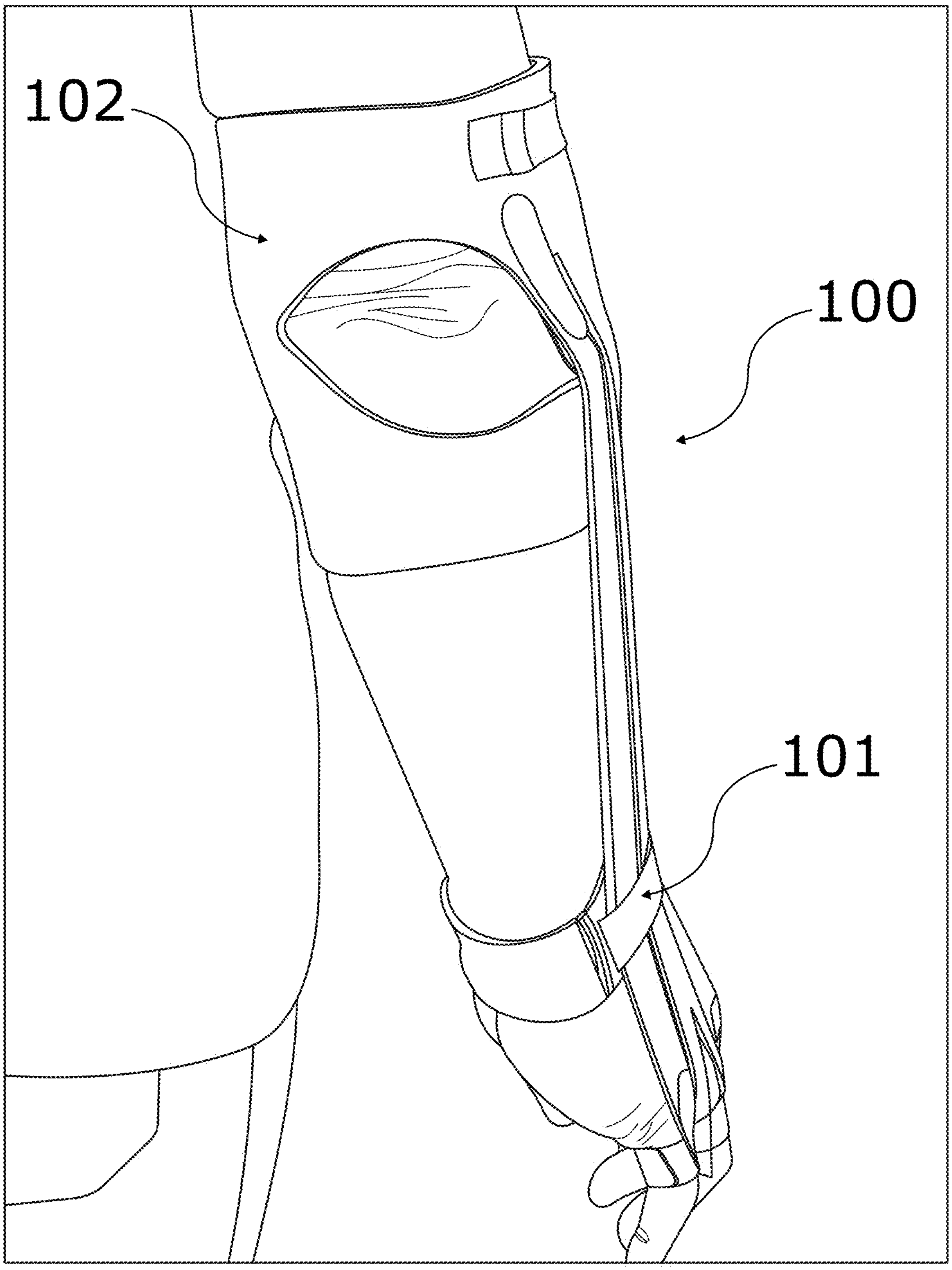
FIG. 9 is a rear arm view of the present invention
Figure 10:
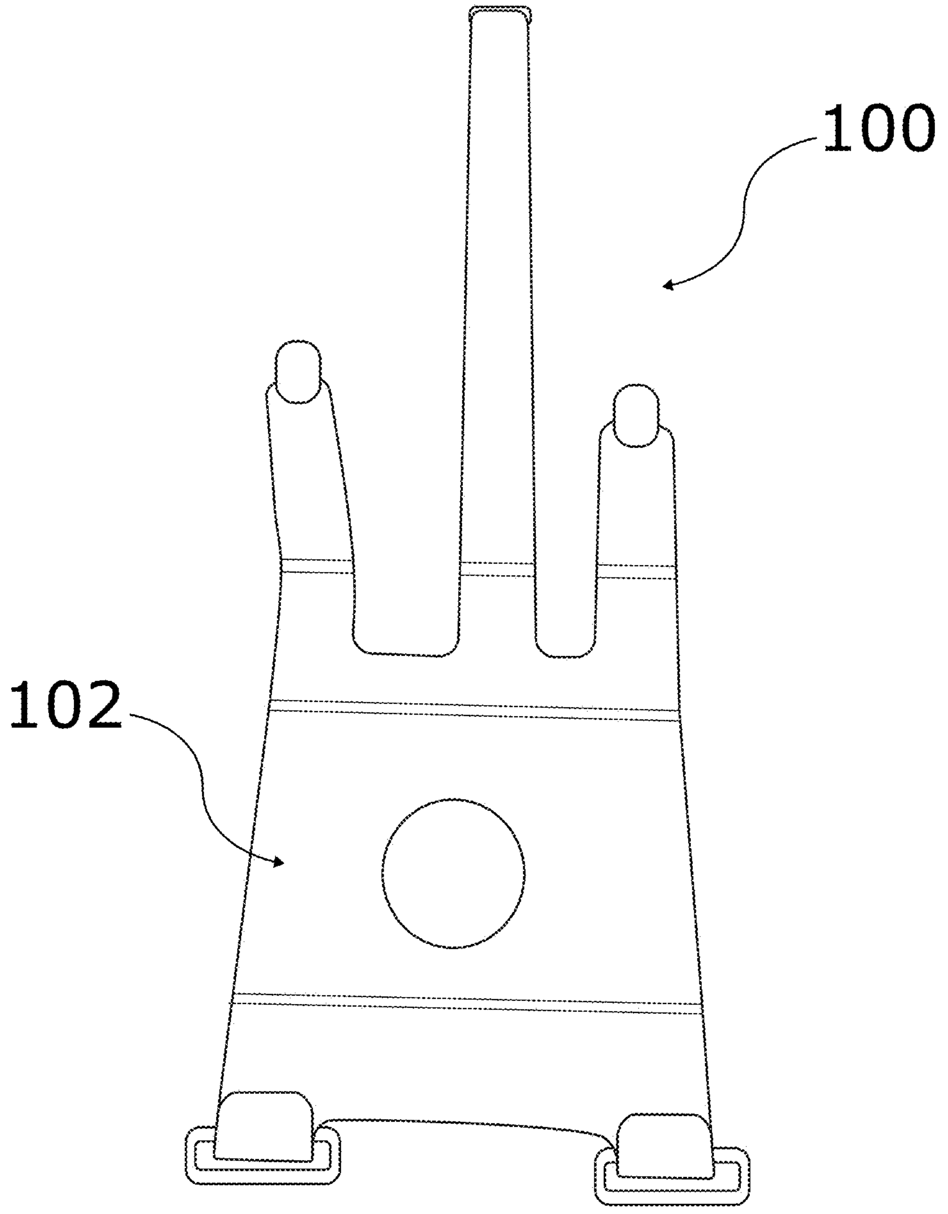
FIG. 10 shows the inside of the elbow support.
Figure 11:
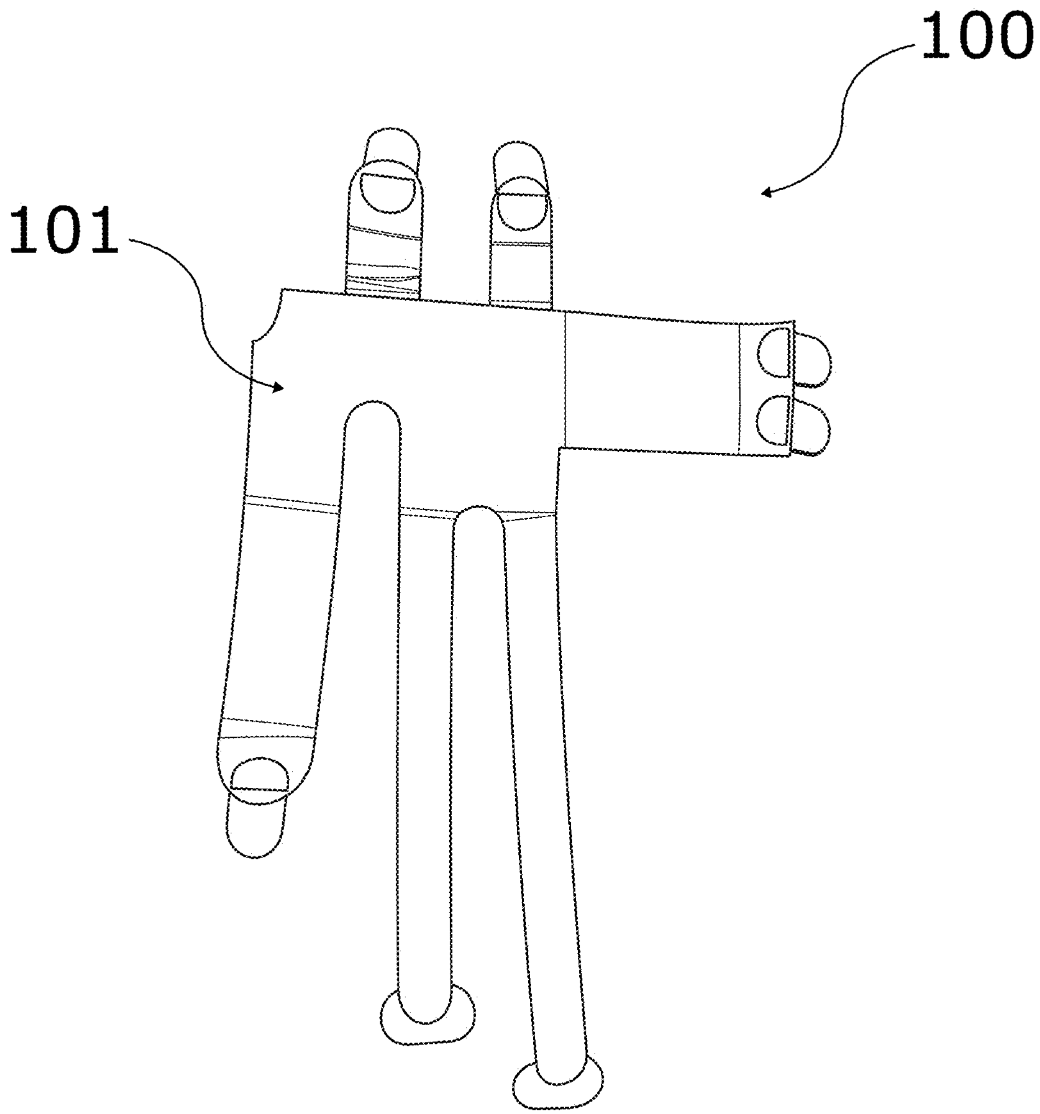
FIG. 11 shows the inside of the hand wrap portion.

The present invention is made of medical-grade materials with elastic properties to ensure it is comfortable and safe to wear and to prevent skin irritation. Said hand wrap 101, as shown in FIG. 5, envelops the hand with multiple attaching points and straps. Said straps may attach using Velcro, sticky material, loops, or other means. Further straps extend upward from the hand to the elbow. Said hand wrap 101 provides normal movement of antagonist muscles so the wrist can move freely, but when the user is not contracting muscles, the hand will return to the extension position without having to contract the extensor muscles. This releases pressure and contraction at the elbow. FIG. 11 shows the hand wrap 101 portion of the present invention. In this orientation, said hand wrap 101 may be used on the left hand to relieve tennis elbow or on the right hand to relieve golfer's elbow. Said hand wrap 101 may be wrapped by the user's other hand or with the assistance of another person. A first tab may be held in place while applying subsequent tabs, and the elastic materials allows the wrap to stretch for the proper fit. In various embodiments, said hand wrap 101 can envelop around a user's thumb.

Figure 4:
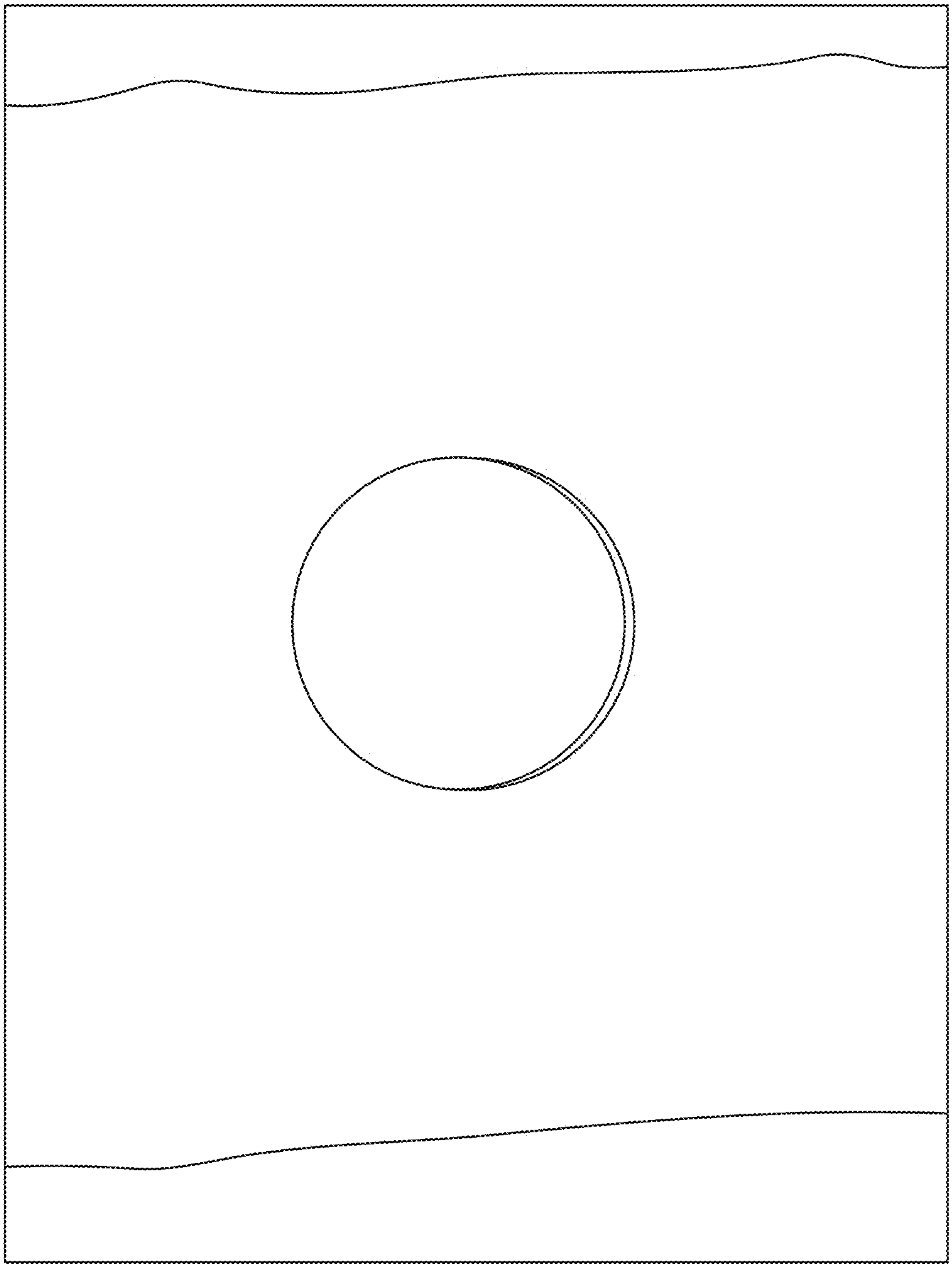
FIG. 4 shows the section of the present invention where the elbow is placed.
Figure 12:
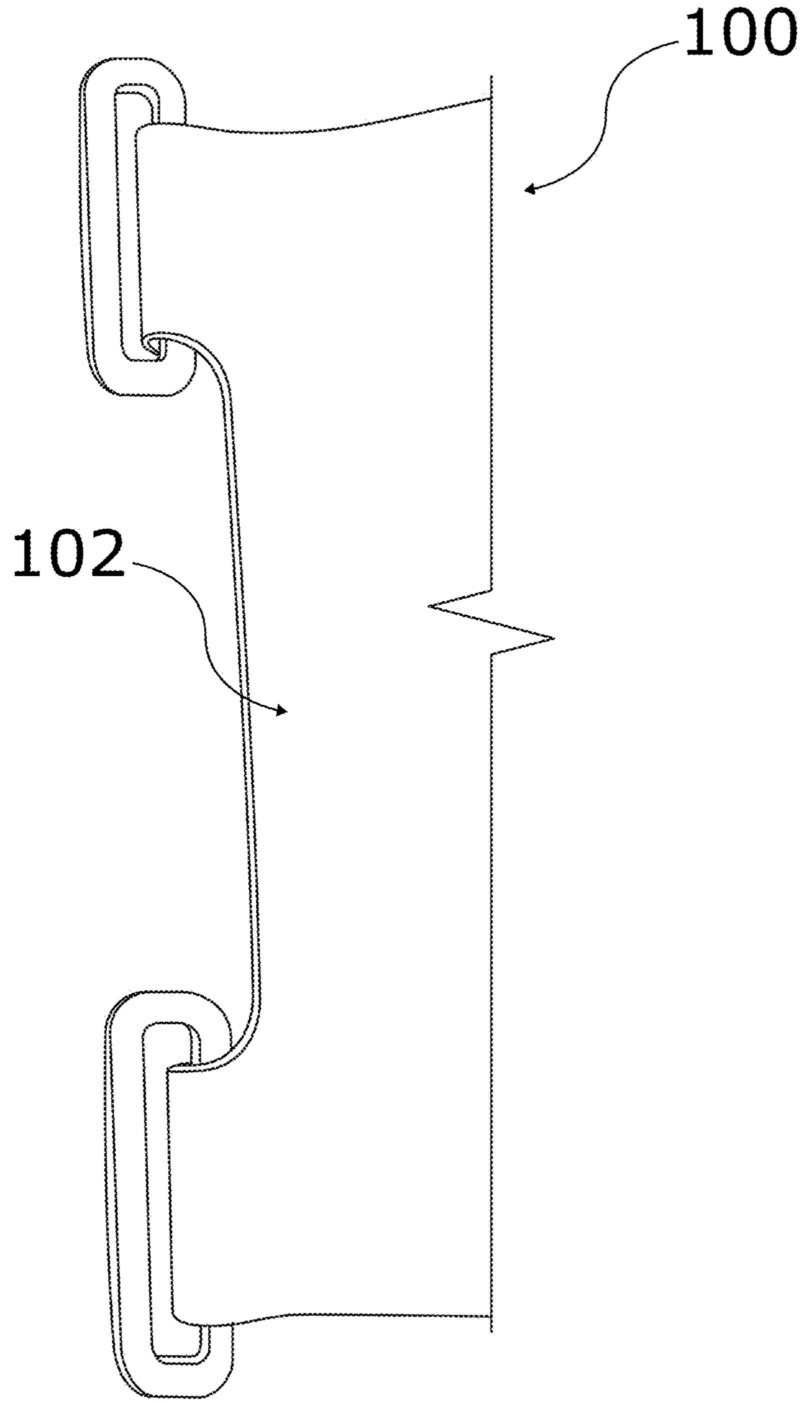
FIG. 12 shows the plastic loops which connect the brace.
Figure 13:
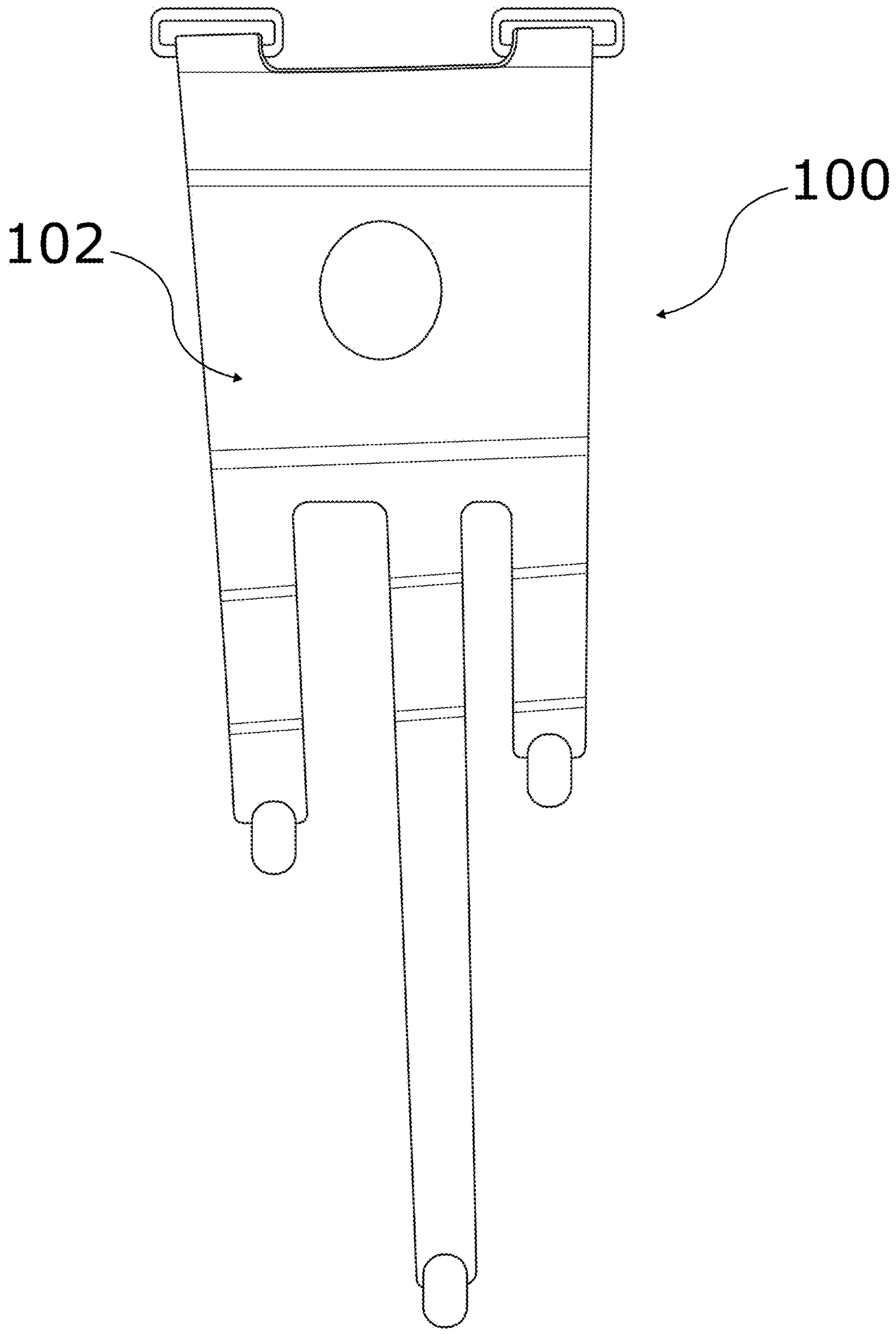
FIG. 13 shows the elbow support with multiple straps, the longest of which may be cut to alter the size and fit.

Said arm wrap 102 can be pulled up to the elbow joint. Straps wrap around the arm, as shown in FIG. 6-9. FIG. 4 shows the hole where the elbow is placed when wrapped around the user's arm, allowing the elbow to be free for flexion and extension. Further external straps may be added if needed. FIG. 12 shows a close-up view of the loops which may be used to connect the straps. Said arm wrap 102 further comprises vibrational motors 103, as shown in FIG. 1. Said vibrational motors 103 are placed around the inflamed tendons to stimulate collagen and eliminate pain. A user may control the vibration electronically, for example via Bluetooth or a smartphone. An EMG sensor 104 such as the one shown in FIG. 2 may also be included to provide biofeedback for muscle tension. Said EMG sensor 104 may be programmed to activate at a given level of muscle contraction or allow the vibration to be controlled manually. Said EMG sensor 104 may be programmed to activate the vibrational motors at a certain muscle tension.

Figure 3:
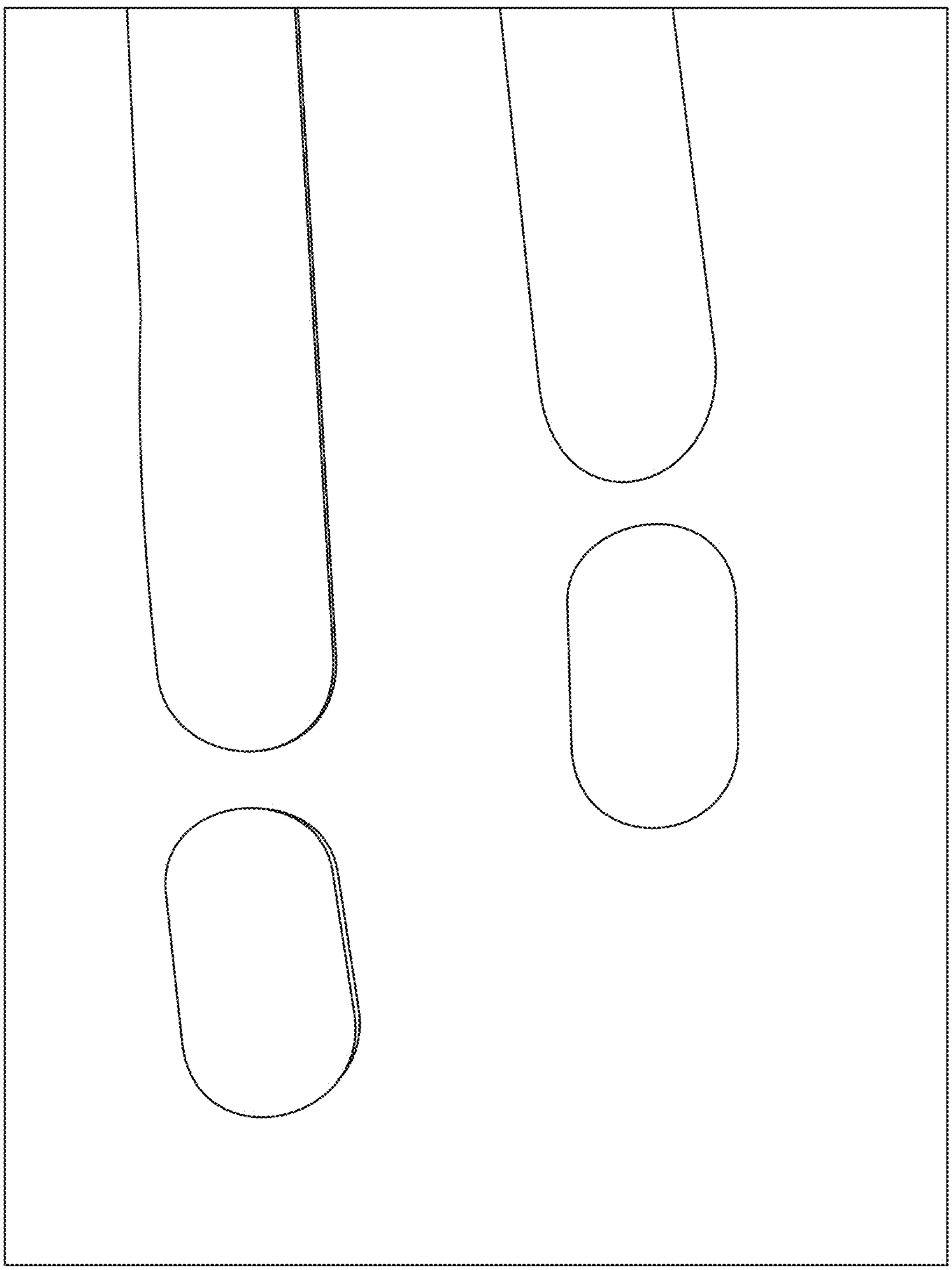
FIG. 3 shows the adjustable straps of the present invention.

Said plurality of straps, such as the ones shown in FIG. 3, connect the hand wrap 101 to the arm wrap 102, and said plurality of straps can be pulled and connected to any part for pronation or supination of the hand. This allows for adjustability to maximize the comfort and effectiveness of the present invention based on the needs of the user.

The present invention 100 holds the forearm muscles in a released or shortened position when using the hand wrap connected to the arm wrap. Said hand wrap 101 may further be used by itself and connected to the elbow via patches on the elbow using glue or other substances. The present invention 100 takes tension off the muscles and tendons where they are attached to the bone and provide relief to the periosteum.

In a preferred embodiment, said hand wrap 101 is a single piece of material providing multiple support points for the user's hand. Said hand wrap 101 provides relief for conditions such as carpal tunnel, tendonitis of the hand and thumb, wrist fatigue, tennis elbow, extensor muscle decontraction, or radial tunnel syndrome. Said hand wrap 101 may be applied using the following steps, but other methods are possible. The user places the hand wrap 101 around the thumb to stretch one tab around the index finger. This holds the wrap in place. Another tab is pulled around the palm of the hand, pulling the material up in between the thumb and index finger to attach the tab to the top of the material on the hand, where it may be received by a hook. A third tab is fixed around the pinky finger or in between the ring and pink finger. This provides decontraction of the extensor carpi ulnaris and an anchor point. A fourth tab is pulled around the base of the thumb and holds the thumb inwards, releasing muscle contraction on the thumb. Two long straps may be pulled up the arm to the elbow and attached. This allows the hand to be pulled toward the elbow to shorten the extensor muscles without contracting them.

Said arm wrap 102 slides over the elbow joint, where a hole is provided to be positioned around the elbow. The straps may be cut to different lengths depending on the length and size of the user's arm. A patch with vibrating motors 103 is located around the tendons of the extensor muscles to repair collagen and soft tissue.

All illustrations show the present invention as applied to a user's right arm. All components of the present invention may be mirrored in order to fit a user's left arm. None of the present disclosure is intended to limit the functionality of the present invention to one arm only. Although the invention has been explained in relation to its preferred embodiment, it is to be understood that many other possible modifications and variations can be made without departing from the spirit and scope of the invention.

What is claimed is:

1. A support brace comprising:

a hand wrap comprising a palm panel, a first tab extending from a first side of the palm panel, a second tab extending from a second side of the palm panel, and a plurality of elastic straps extending from the palm panel; and an elbow wrap comprising a body having a posterior opening, a proximal strap, a middle strap, and a distal strap extending from a first side of the body, wherein a first inner opening is defined by a first edge of the body, the proximal strap, the middle strap, and a second edge of the body opposite the first edge, wherein a second inner opening is defined by the first edge of the body, the middle strap, the distal strap, and the second edge of the body opposite the first edge, and wherein the posterior opening is positioned between the middle strap and the distal strap;

wherein the plurality of elastic straps of the hand wrap interconnects the hand wrap and the elbow wrap at a plurality of positions along the elbow wrap;

wherein the plurality of elastic straps maintain tension between the hand wrap and the elbow wrap to urge the hand wrap toward the elbow wrap; and wherein the middle strap retains the elbow wrap against displacement toward the hand wrap when the plurality of elastic straps urges the hand wrap toward the elbow wrap.

2. The support brace of claim 1, wherein the plurality of elastic straps is connectable to a plurality of positions along the elbow wrap.

3. The support brace of claim 1, wherein the plurality of elastic straps is adjustable in length by cutting.

4. The support brace of claim 1, wherein the plurality of elastic straps connects to the elbow wrap through a plurality of loop fasteners.

5. The support brace of claim 1, wherein the hand wrap further comprises a first finger anchor tab and a second finger anchor tab extending from the palm panel, each finger anchor tab comprising a hook and loop fastening tab at a terminal end thereof.

6. The support brace of claim 5, wherein the hand wrap further comprises a palm tab extending from the palm panel.

7. The support brace of claim 5, wherein the first finger anchor tab is configured to extend around an index finger.

8. The support brace of claim 7, wherein the second finger anchor tab is sized to extend around a pinky finger.

9. The support brace of claim 7, wherein the second finger anchor tab is sized to extend between a ring finger and a pinky finger.

10. The support brace of claim 1, wherein the hand wrap further comprises a thumb loop extending from the palm panel.

11. The support brace of claim 1, further comprising a detachable patch removably attachable to the elbow wrap, the detachable patch comprising a plurality of vibrational motors, a circuit board, and a power source.

12. The support brace of claim 11, wherein the circuit board further comprises a wireless communication module operative to receive signals from an external device to regulate an intensity of the plurality of vibrational motors.

13. The support brace of claim 11, further comprising a plurality of electromyography sensors positioned on the elbow wrap, wherein the electromyography sensors are operative to detect muscle tension and activate the plurality of vibrational motors at a predetermined level of muscle tension.

14. A support brace comprising:

a hand wrap comprising a palm panel, a first tab extending from a first side of the palm panel, a second tab extending from a second side of the palm panel, and a plurality of elastic straps extending from the palm panel; and an elbow wrap comprising a body having a posterior opening, a proximal strap, a middle strap, and a distal strap extending from a first side of the body, wherein a first inner opening is defined by a first edge of the body, the proximal strap, the middle strap, and a second edge of the body opposite the first edge, wherein a second inner opening is defined by the first edge of the body, the middle strap, the distal strap, and the second edge of the body opposite the first edge, wherein the posterior opening is positioned between the middle strap and the distal strap, and wherein the middle strap is offset toward the proximal strap such that the first inner opening is smaller than the second inner opening;

wherein the plurality of elastic straps of the hand wrap interconnects the hand wrap and the elbow wrap at a plurality of positions along the elbow wrap;

wherein the plurality of elastic straps maintain tension between the hand wrap and the elbow wrap to urge the hand wrap toward the elbow wrap; and wherein the middle strap retains the elbow wrap against displacement toward the hand wrap when the plurality of elastic straps urges the hand wrap toward the elbow wrap.

15. The support brace of claim 14, wherein the plurality of elastic straps are coupled to the hand wrap and releasable connected to the elbow wrap such that the hand wrap is removable from the elbow wrap independently of the elbow wrap, and wherein the hand wrap is re-attachable to the elbow wrap in a reversed orientation to reposition the plurality of elastic straps along the elbow wrap.

16. A support brace comprising:

a hand wrap comprising a palm panel, a first tab extending from a first side of the palm panel, a second tab extending from a second side of the palm panel, and a plurality of elastic straps extending from the palm panel, wherein each of the first tab, the second tab, and the plurality of elastic straps comprises a hook and loop fastener at a terminal end thereof; and an elbow wrap comprising a body having a posterior opening, a proximal strap, a middle strap, and a distal strap extending from a first side of the body, a first ring coupled to the body through which the proximal strap passes and doubles back to fasten to the body via a hook and loop fastener, and a second ring coupled to the body through which the distal strap passes and doubles back to fasten to the body via a hook and loop fastener, wherein a first inner opening is defined by a first edge of the body, the proximal strap, the middle strap, and a second edge of the body opposite the first edge, wherein a second inner opening is defined by the first edge of the body, the middle strap, the distal strap, and the second edge of the body opposite the first edge, wherein the posterior opening is positioned between the middle strap and the distal strap, and wherein the middle strap is offset toward the proximal strap such that the first inner opening is smaller than the second inner opening;

wherein the plurality of elastic straps of the hand wrap interconnects the hand wrap and the elbow wrap at a plurality of positions along the elbow wrap;

wherein the plurality of elastic straps maintain tension between the hand wrap and the elbow wrap to urge the hand wrap toward the elbow wrap; and wherein the middle strap retains the elbow wrap against displacement toward the hand wrap when the plurality of elastic straps urges the hand wrap toward the elbow wrap.

17. The support brace of claim 16, wherein the plurality of elastic straps are positioned along a posterior side of the support brace between the hand wrap and the elbow wrap.

18. The support brace of claim 16, wherein the plurality of elastic straps are positioned along an interior side of the support brace between the hand wrap and the elbow wrap.

* * * * *